(12) United States Patent
Hinshon

(10) Patent No.: US 7,018,350 B2
(45) Date of Patent: Mar. 28, 2006

(54) METHODS OF MAKING AND USING AN ANKLE-FOOT ORTHOSIS

(76) Inventor: Patrick Scott Hinshon, 748 Linden Cir. South, Maplewood, MN (US) 55119

( * ) Notice: Subject to any disclaimer, the term of this patent is extended or adjusted under 35 U.S.C. 154(b) by 61 days.

(21) Appl. No.: 10/353,841

(22) Filed: Jan. 28, 2003

(65) Prior Publication Data

US 2003/0153852 A1 Aug. 14, 2003

Related U.S. Application Data

(60) Provisional application No. 60/351,511, filed on Jan. 28, 2002.

(51) Int. Cl.
*A61F 5/00* (2006.01)
(52) U.S. Cl. .......................... 602/16; 602/26
(58) Field of Classification Search .............. 602/5, 602/16, 20, 23, 26, 27–29; 128/882
See application file for complete search history.

(56) References Cited

U.S. PATENT DOCUMENTS

| 5,022,390 A | * | 6/1991 | Whiteside | ...... 607/2 |
| 5,328,444 A | * | 7/1994 | Whiteside | ...... 602/16 |
| 5,897,514 A | * | 4/1999 | Currier | ...... 602/16 |

\* cited by examiner

*Primary Examiner*—Michael A. Brown

(57) ABSTRACT

The present invention is directed, to an improved orthosis and posterior plantar flexion stop for the orthosis, as well as to methods of making and using the orthosis and posterior stop, plus components used to make the orthosis and stop. The ankle-foot orthosis and plantar flexion stop of the present invention improve on the function and performance of the orthosis, while also making the orthosis attractive and easier to use than prior devices.

7 Claims, 8 Drawing Sheets

US 7,018,350 B2

METHODS OF MAKING AND USING AN ANKLE-FOOT ORTHOSIS

PRIORITY

This application claims priority to U.S. provisional patent application Ser. No. 60/351,511 filed 28 Jan. 2002.

FIELD OF THE INVENTION

The present invention is directed to an improved ankle-foot orthosis, an improved posterior plantar stop for the orthosis, methods of making the orthosis and posterior stop, materials used to form the orthosis and posterior stop, and therapeutic procedures using the orthosis and posterior stop.

BACKGROUND OF THE INVENTION

The human foot is designed so that it can rotate and pivot with regard to the lower leg, and such movements are essential to walking. One primary movement is plantar flexion, which is downward motion of the foot that occurs in the sagittal plane. In some circumstances it is necessary to limit plantar flexion to less than 90 degrees. For example, individuals with paralysis or weakness of the dorsi flexion muscle group (which lifts the foot) typically have trouble raising their foot, such as when they're walking. This dorsi flexion problem can result in tripping and falling as the front of the foot catches on obstacles. Also, individuals with excessive plantar flexion sometimes compensate when walking by lifting their foot and leg higher than normal in order to lift the front of their foot off of the ground. This unnatural lifting of the leg and foot results in a modified gait that is sometimes referred to as a steppage gait because it bears resemblance to the gait of a high-stepping horse. Walking with a steppage gait is inefficient and tiresome, and can also lead to other undesirable stresses on the body.

Various ankle-foot orthosis devices have been developed to prevent excessive plantar flexion. For example, a solid ankle brace can be placed in an individual's shoe so as to prevent flexing at the ankle joint. These braces may be improved upon by allowing a pivoting movement at the ankle joint to permit the angle between the foot and lower leg to decrease in size, while using a stop to prevent the foot from exceeding a 90 degree angle with the lower leg. These improved articulating orthosis offer significant advantages over prior rigid devices, including improved comfort, allowing a more natural walking motion by the patient, and reducing stiffness by promoting flexing of the ankle joint.

A number of companies currently make articulating orthosis and components for these orthosis, including components for the ankle joints and posterior stops. Unfortunately, many of these adjustable ankle-foot orthosis have significant shortcomings. For one, manufacture of the posterior stop is often time consuming and tedious, involving careful alignment of small components that must be delicately adjusted after installation. In addition, these posterior stops are often much larger and less attractive than desired. The problems with the large size of the stops are not limited to aesthetics, because their large size generally requires that at least part of the stop extend below the back of the shoe. Also, the stops are so large that they do not comfortably fit within a shoe, and patients frequently need two pairs of shoes of different sizes, or must modify their shoes (such as by removing part of the shoe's back or stretching the shoe to make it larger) to permit wearing of these orthosis with large posterior stops.

Therefore, a need exists for an improved ankle-foot posterior orthosis that is less cumbersome to make and use, while also being attractive, durable, and small.

SUMMARY OF THE INVENTION

The present invention is directed, in part, to an improved orthosis and posterior plantar flexion stop for the orthosis, as well as to methods of making and using the orthosis and posterior stop, plus components used to make the orthosis and stop. The ankle-foot orthosis and plantar flexion stop of the present invention improve on the function and performance of the orthosis, while also making the orthosis attractive and easier to use than prior devices.

The improved orthosis has a compact, adjustable, easily manufactured stop that is both durable and functional. Manufacture of the orthosis and stop utilizes a three dimensional molding blank configured for easy and precise fabrication and positioning on the orthosis. As described below, the molding blank is used to form a cavity in the walls of the orthosis for retaining a stopping bumper, while also forming a bumper rest with which the stopping bumper makes contact.

The improved ankle-foot orthosis and posterior stop also significantly reduce or eliminate the clicking noise created by existing orthosis stops. This reduction in noise is accomplished by using a superior thermomolded composition well suited to the functions necessary for a posterior stop. Thus, the improved orthosis and stop are able to be relatively quiet, yet allow precise sagittal adjustability and durability.

Other benefits of the improved orthosis and stop include the ability to produce a very compact posterior stop that decreases the length, width, and thickness necessary to produce a functioning stop. In particular, the width and thickness of the posterior stop can be significantly reduced, while the length can also be limited. In addition to limiting the length of the stop, the position of the stop components can be improved so that they do not excessively intrude into a shoe of a patient. In doing so the invention results in a more attractive and comfortable orthosis that is well received by patients.

The compact stop is also a major functional improvement because it permits a patient greater freedom in choosing footwear, while maintaining sagital alignment over time in relationship to the durability of the materials used to make the orthosis and stop. Many current orthosis stops are so bulky, and positioned so low along a patient's ankle, that they significantly intrude into a patient's shoe. These bulky stops often necessitate buying two pairs of shoes of different sizes, modification of shoes to allow for the bulky stop, or limitations on what kind of shoes are worn. The present invention significantly reduces or eliminates the need to make these adjustments in a patient's footwear.

A further aspect of the present invention is that adult patients can temporarily remove the bumper of the posterior stop in order to drive an automobile or perform other acts that require plantar flexion of more than 90 degrees, and then easily reinsert the motion stop to restore its function for ambulation. This modification is significant because it allows a patient to perform important daily routines with minimum intrusion and no sensitive adjustment or alignment of the motion stop. Also, different bumpers can be interchanged to create different stop angles, including shorter bumpers that allow some posterior flexion. Such bumpers are useful when wearing footwear that has the heel elevated slightly above the front of the foot. Without such bumper stops a patient will sometimes resort to unnatural knee-bending when wearing these inclined shoes. Yet another further improvement of the invention is that it can be used to increase dorsi flexion in patients by providing customized, precise nocturnal gastroc stretch, in which the amount of stretch can be precise and customized.

Other features and advantages of the invention, including methods of making an orthosis, will be apparent from the following detailed description of the invention and the claims. The above summary of principles of the disclosure is not intended to describe each illustrated embodiment or every implementation of the present disclosure. The detailed description that follows more particularly exemplifies certain embodiments utilizing the principles disclosed herein.

BRIEF DESCRIPTION OF THE DRAWINGS

The invention will be more fully explained with reference to the following drawings.

Figure 1:
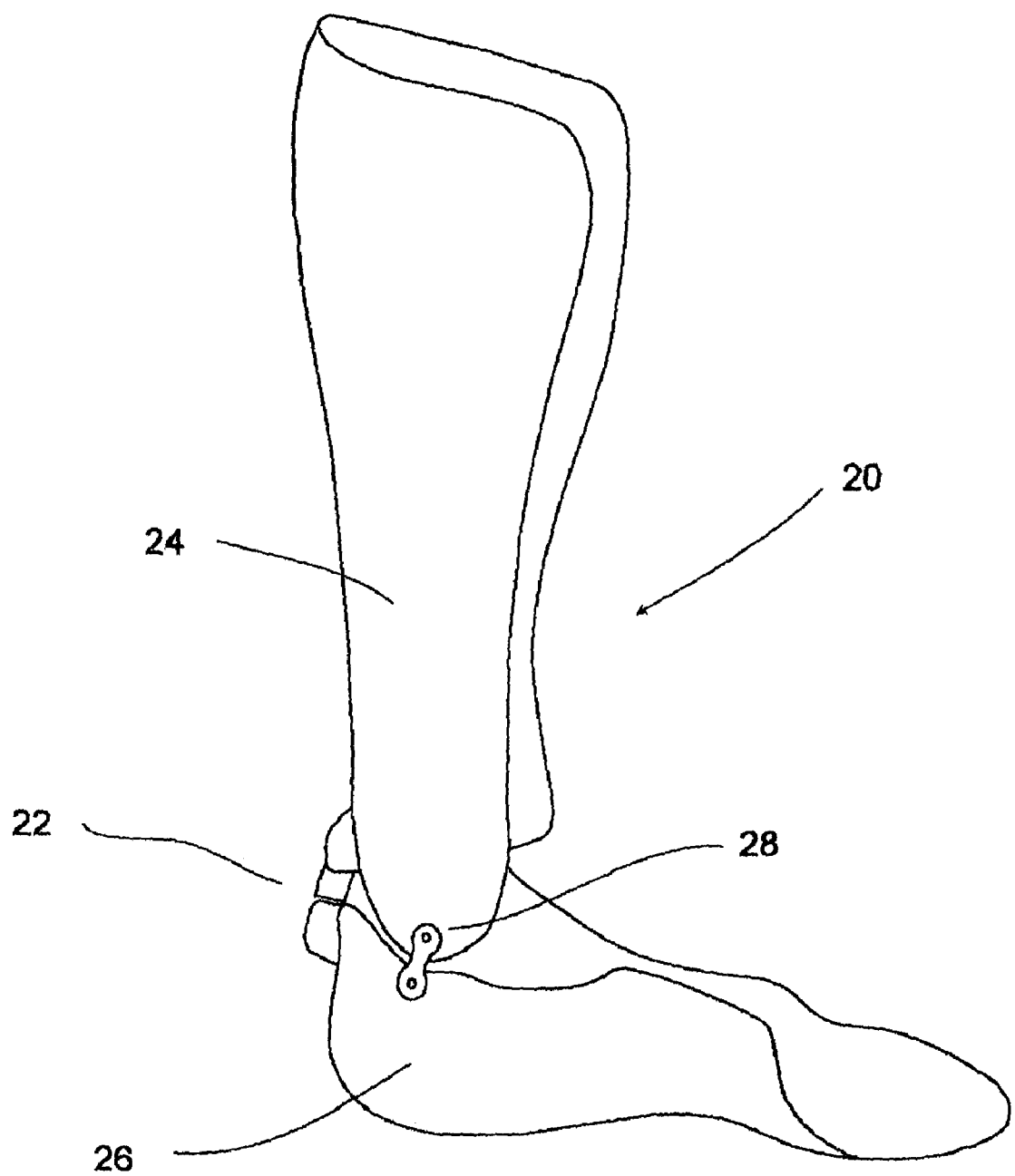
FIG. 1 shows a simplified side perspective view of an ankle-foot orthosis, the orthosis having a posterior plantar flexion stop constructed and arranged in accordance with an implementation of the invention.

While principles of the invention are amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure and claims.

DETAILED DESCRIPTION OF THE INVENTION

Stop mechanisms, also referred to as plantar stops and motion limiters, made in accordance with the invention generally restrict the motion of an ankle-foot orthosis by limiting plantar flexion. The stop mechanisms of the present invention are particularly useful because they are designed as part of a complete system that allows for the creation of particularly small, but highly functional, posterior plantar stops. In addition, the plantar stops can be made easily with a minimum of steps and tools, and can be produced quickly.

The stop mechanisms typically include a removable stopping bumper configured to contact a bumper rest, the removable stopping bumper comprising a head and a stem, the head configured to contact the bumper while the stem is configured for insertion into a cavity in an orthosis. The stopping bumper is removable from the cavity in the orthosis so that it can be replaced with a bumper of a different thickness in order, for example, to allow a patient greater plantar flexion for some activities (such as driving a car), in order to accommodate different footwear, or to promote therapeutic nocturnal gastroc stretch.

Generally the bumper head has a larger horizontal cross section than the bumper stem. The bumper rest typically comprises a surface configured for receiving the bumper head, and this surface contains a portion of an exposed molding blank partially surrounded by a thermoformed wall. The thermoformed wall partially surrounding the molding blank is usually contiguous and integrally formed with the wall of the orthosis from a single piece of thermoplastic material. Indeed, the molding blank is generally configured so that it is not necessary to use anything other than the wall of the orthosis to hold the blank in place. In this regard it is possible to hold the blank in place without using extra pieces of thermoforming material.

In most implementations the molding blank is not entirely surrounded by the thermoformed wall because those portions of the molding blank that were originally in contact with the mold during thermal forming of the orthosis are not surrounded by thermoformed wall. Thus, part of the molding blank can be left exposed on the interior of the orthosis. However, the molding blank does not fall out of the exposed gap in the wall because the molding blank has a shape that is wider at its posterior than this exposed gap that is formed at its anterior.

Aspects of the invention will be better understood by reference to the figures. FIG. 1 shows an articulating ankle-foot orthosis 20 incorporating a plantar flexion stop 22 constructed and arranged in accordance with the invention. The orthosis 20 has an upper portion 24 configured to retain a patient's lower leg, plus a lower portion 26 configured to retain a patient's foot. Ankle joint 28 allows the upper and lower portions 24, 26 of the orthosis 20 to pivot with respect to one another, typically along an axis that corresponds substantially to the axis of the patient's own ankle. The plantar flexion stop 22 restricts excessive flexing of the foot by preventing plantar flexion at an angle greater than 90 degrees between the foot and lower leg (with some exceptions wherein slightly greater than 90 degree extension is desired). The flexion stop 22 of the invention provides a compact, yet durable, stop that is easy to manufacture, uniquely adjustable, and aesthetically pleasing.

Figure 2A:
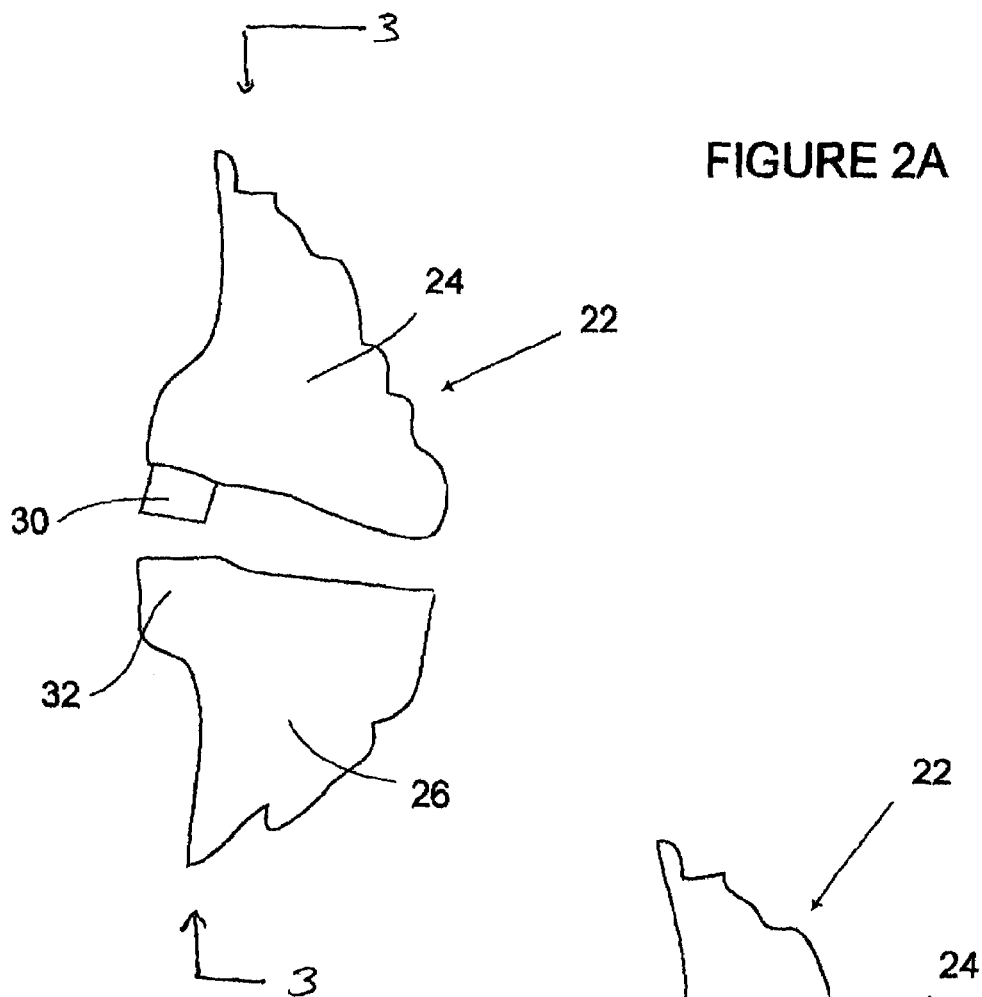
FIG. 2A shows an enlarged partial view of the plantar flexion stop of FIG. 1, with the orthosis in a dorsi flexion position and the stop not engaged.
Figure 2B:
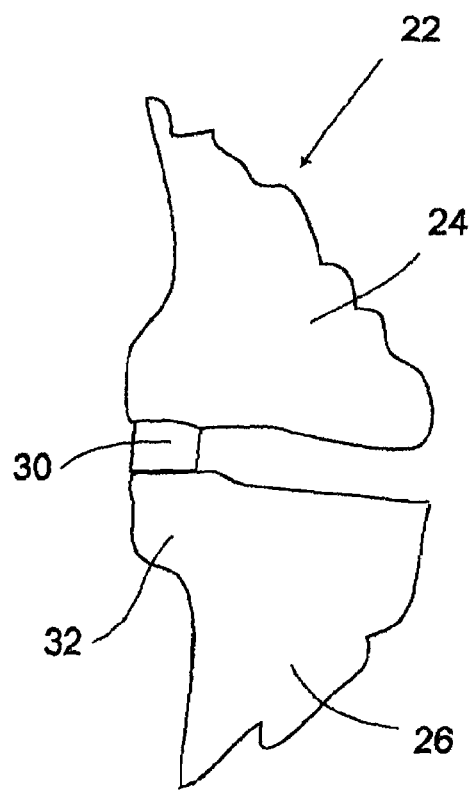
FIG. 2B shows an enlarged partial view of the posterior plantar flexion stop of FIG. 1, showing the orthosis in a neutral flexion position with the stop engaged.

In reference now to FIGS. 2A and 2B, a plantar flexion stop 22 made in accordance with the invention is shown in closeup view with a portion of the orthosis also shown in cut-away views. The posterior flexion stop 22 has two primary elements: a removable stopping bumper 30 and a bumper rest 32. In general, the stopping bumper 30 is positioned above the bumper rest 32 (although the opposite arrangement is also possible). Stopping bumper 30 typically snaps in place into a cavity or groove formed within the thermoformed wall of the upper portion 24 of the orthosis. Bumper rest 32 is positioned within the wall, and indeed comprises part of the wall, of the lower portion 26 of the orthosis. In most, but not all, implementations of the invention, the bumper rest 32 is not removable from the orthosis 20, unlike the stopping bumper 30. FIG. 2A shows the orthosis and foot in a dorsi flexion position, wherein there is a gap between the stopping bumper 30 and bumper rest 32. FIG. 2B shows the orthosis and foot in a neutral flexion position, with stopping bumper 30 in contact with the bumper stop 32, thereby preventing plantar flexion.

Figure 3A:
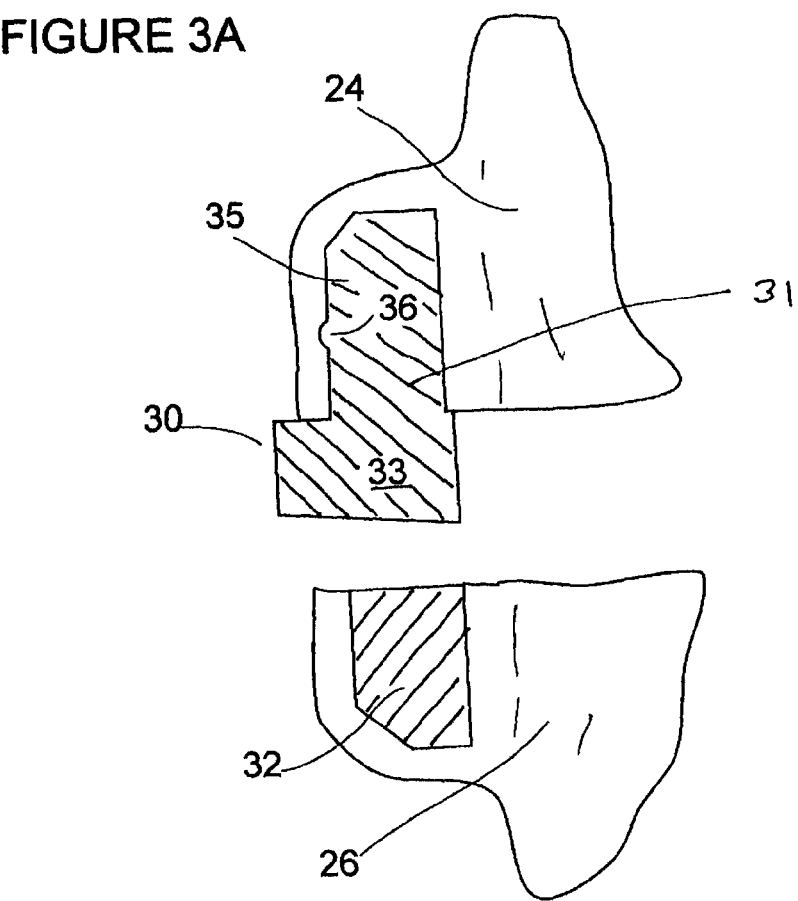
FIG. 3A shows an enlarged cross sectional view of a posterior plantar flexion stop, the cross section taken along lines 3—3 of FIG. 2A.
Figure 3B:
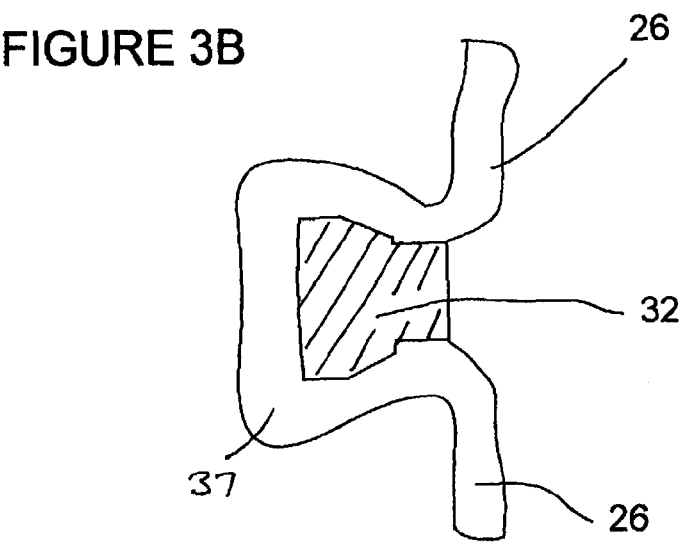
FIG. 3B shows an enlarged top view of the top of the bumper rest of FIG. 3A.

The specific elements of the plantar flexion stop 22 are shown in more detail in FIGS. 3A and 3B. FIG. 3A is a vertical cross-section of a stopping bumper 30 and bumper rest 32 made in accordance with an implementation of the invention. FIG. 3B is a top view of a bumper rest 32 made in accordance with the invention. The stopping bumper 30 in the depicted embodiment includes a stem 31 and a head 33. The head 33 is configured to make contact with the bumper rest 32 in order to stop plantar flexion. The stem 31 is designed such that it can be snapped in place within a channel 35 formed on the inside of the upper portion 24 of the orthosis. This channel 35 is typically formed using a molding blank, which is removed and replaced with the stem 31. In some implementations a bump or ridge 36 is made in the stem 31, this bump or ridge 36 is configured to engage a corresponding depression in cavity 35, thereby helping to keep the stopping bumper 30 in place. Multiple bumps or ridges 36 can be used in a cavity to promote engagement of the stem 31 in the cavity 35.

The stem 31 is tightly held within cavity 35. Typically, the stem 31 is held in place on at least three sides by the thermoformed material that forms the rest of the orthosis described herein. In some implementations the thermoformed material is nearly as thick as the stem, while in other implementations the stem is considerably thicker than the thermoformed material. The bumper head 33 extends out from the cavity, and is typically considerably wider than the stem 31. Also, bumper head 33 generally extends beyond the perimeter of the stem so as to substantially overlap portions of the of wall the upper portion 24 of the orthosis that forms cavity 35. Heads 33 of various thicknesses can be used to form the stopping bumper 30. In addition, the head 33 is typically constructed of a material that can be ground down or cut if necessary to optimize fit and comfort for a patient. Opposite the stopping bumper 30 is the bumper rest 32. The top of the bumper rest 32 typically has exposed portions of a molding blank that have been at least partially encased within the wall 37 of the bottom 26 of the orthosis. Manufacture of this integrated bumper rest 32 is described in greater detail below.

The invention is further directed to an improved orthosis for an ankle-foot joint, the orthosis comprising a first portion configured to be secured to the foot of a patient; a second portion configured to be secured to the lower leg of a patient; a joint configured to allow the first portion and second portion to pivot with regard to one another; and a stop mechanism positioned on the posterior of the orthosis, the stop mechanism comprising a bumper and a bumper rest; wherein the bottom of the stop mechanism is positioned above the axis of rotation in the sagittal plane of the ankle. It will be appreciated that the distance above the axis of rotation of the ankle will vary depending upon the size of the brace, and thus the absolute distance will often be quite small on a pediatric brace compared to an adult brace. However, in some implementations the stop mechanism is positioned at least 1.0 centimeter above the axis of rotation in the sagittal plane of the ankle, more desirably at least 2.0 centimeters, and even more desirably at least 2.5 centimeters above the axis of rotation in the sagittal plane of the ankle. In some implementations this distance is greater than 4.0 centimeters above bottom of the orthosis. Also, the compact stop mechanism, and in particular the compact bumper rest, allows for placement of the bottom of the bumper stop relatively high off the bottom of the orthosis, thereby permitting a patient to have greater options in what kind of footwear the will use.

One of the significant aspects of the present invention is that it allows a motion stop to be made that is extremely compact. This can be accomplished, in part, by configuring a minimally sized cavity or recess in the wall of the orthosis for retaining the stem of the head of the stopping bumper, while also permitting the use of a small bumper rest. Rather than surrounding the stem on all sides, thereby necessitating a thick stop, the present invention permits forming a cavity in the wall of the orthosis that does not entirely encase the interior of the stem, thereby reducing the overall thickness of the stop without reducing performance.

While the actual dimensions of the stop mechanism will vary with the size of the orthosis and the thickness of the thermoformed walls of the orthosis, in some implementations the bumper rest has a width measured perpendicular to the sagittal plane of approximately 3 times the thickness of the wall of the orthosis proximate the stop mechanism. Indeed, in certain embodiments, the bumper rest can have a width measured perpendicular to the sagittal plane of approximately 2 to 4 times the thickness of the wall of the orthosis proximate the stop mechanism. Generally this width is not less than two times the thickness of the wall of the orthosis, because the stop contains two sides formed from the same sheet. Also, to keep the stop mechanism compact, it is often desirable that the bumper rest have a width measured perpendicular to the sagittal plane of less than 4 times the thickness of the wall of the orthosis proximate the stop mechanism.

Similarly, the posterior stop desirably has a relatively small overall thickness as measured parallel to the sagittal plane. This thickness can be, for example, approximately 3 or less times the thickness of the wall of the orthosis proximate the posterior stop. In some implementations the thickness measured parallel to the sagittal plane is less than 2.5 times the thickness of the wall of the orthosis proximate the stop mechanism, while in certain implementations this distance is less than 2.0 times the thickness of the wall.

The length (also referred to as height) of the entire stop mechanism is generally also kept to a minimum, although this dimension is sometimes less important than width and thickness of the stop because it has a lesser impact on comfort and footwear choices. Thus, the stop mechanism typically has a vertical length significantly less than 7 centimeters, more typically less than 5 centimeters, and desirably less than 4 or 3 centimeters. The individual components of the stop mechanism, such as the stopping bumper and bumper rest, are similarly slight in size. For example, the bumper rest can have a length that is less than 5 times the thickness of the wall of the orthosis proximate the stop mechanism, alternatively less than 4 times the width of the wall of the orthosis proximate the stop mechanism, and even less than 3 times the width of the wall of the orthosis proximate the stop mechanism.

One aspect of the present invention is an improved molding blank used to form a cavity in the posterior of an orthosis for insertion of the stopping bumper, as well as to assist in the formation of the bumper rest. The molding blank is typically an elongate piece of plastic having an upper end and a lower end. In some embodiments a cut indicator is placed in the body of the molding blank, the cut indicator visible after forming of the wall of the orthosis, and providing an indication of where the partially formed orthosis should be cut to form a two-part orthosis. The cut indicator can comprise, for example, a hole through the body of the molding blank. Also, the molding blank can include a grind indicator in the body of the molding blank, the grind indicator visible after forming of the wall of the orthosis, and providing an indication of how much of the orthosis should be removed during processing after the two pieces of the orthosis have been cut apart. The grind indicator can be, for example, a horizontal bar across the body of the molding blank. In some implementations the molding blank further comprises a recess (or protrusion) configured to receive a tool for removing at least a portion of the molding blank from the orthosis, such as a recess configured to receive a screw driver for forcing out a portion of the molding blank from the orthosis.

Figure 4A:
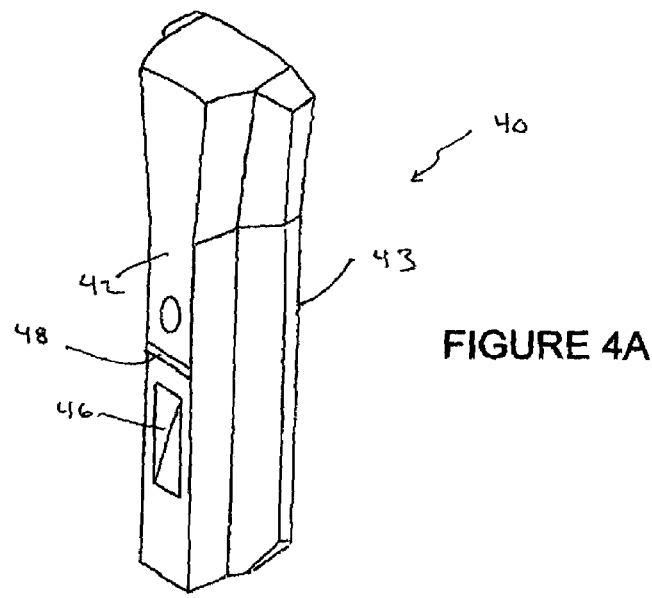
FIG. 4A shows an enlarged perspective view of a molding blank for a plantar flexion stop made in accordance with an implementation of the invention.
Figures 4B, 4C:
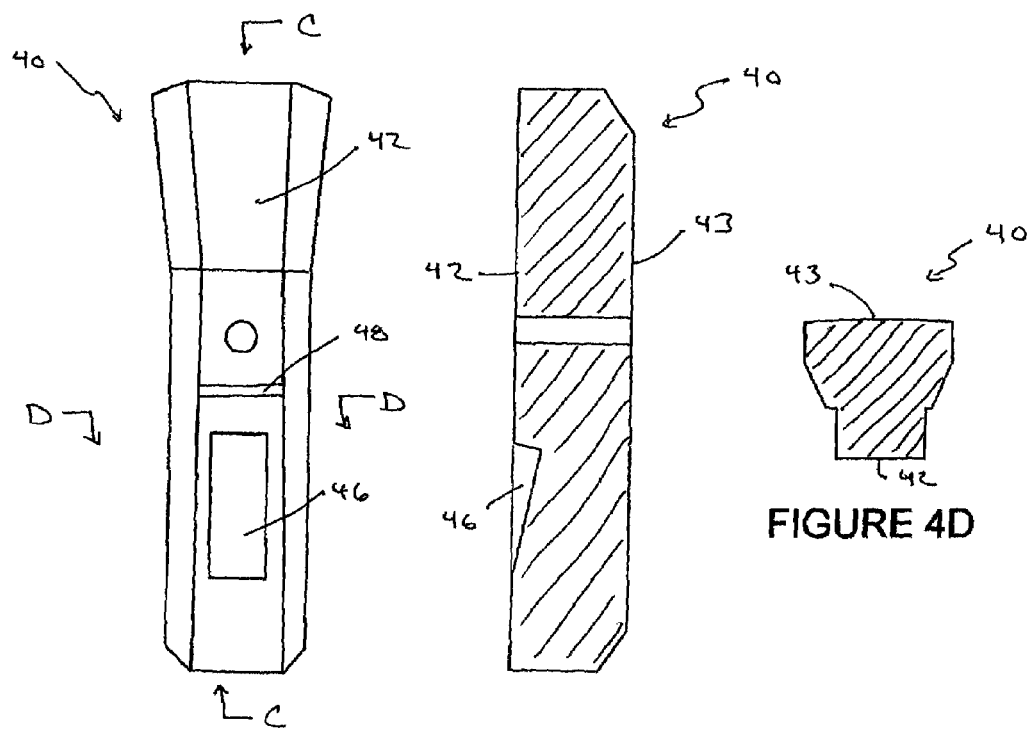
FIG. 4B shows an anterior view of a molding blank for a plantar flexion stop made in accordance with an implementation of the invention.
FIG. 4C shows an enlarged cross sectional view of the molding blank of FIG. 4A, the cross section taken along line C—C of FIG. 4B.
Figure 4D:
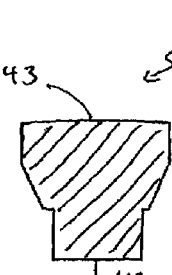
FIG. 4D shows an enlarged cross sectional view of the molding blank of FIG. 4A, the cross section taken along line D—D of FIG. 4B.

Details of a molding blank 40 manufactured in accordance with the invention are shown in FIGS. 4A to 4D. FIG. 4A shows a perspective view of the molding blank 40. FIG. 4B shows an anterior view of the molding blank 40. FIG. 4C shows a cross-section of the molding blank along the sagittal plane. FIG. 4D is a horizontal cross-section. The molding blank 40 shown in these figures can be used to produce a plantar stop that has one removable portion (the bottom of the blank as shown in FIG. 4A). Thus, with this molding blank approximately half of the blank is left within the orthosis to form a portion of the bumper rest. Alternatively, in some implementations the molding blank 40 has two removable portions, thereby allowing the formation of two cavities for receiving stems of bumper stops. Molding blank 40 of FIG. 4A has a narrow side 42 and a wide side 43. This narrow side 42 is generally placed such that it is facing a foot mold during thermoforming of the orthosis. In most implementations the narrow side 42 is in actual contact with the foot mold during thermoforming. Thus, this narrow face is not covered by thermoplastic material after thermoforming of the orthosis (see FIG. 3B). Indeed, this narrow face is left exposed in part to gain access to it for easy removal from the orthosis to produce a cavity for a stem of a stopping bumper. The molding blank is retained within the cavity of the orthosis because the wide side 43 is encased in the thermoplastic material, and this wide side 43 cannot readily fit through the opening in a cavity formed by the exposed narrow side 42.

In addition, molding blank 40 includes a tool slot 46 configured to aid in the removal of portions of the molding blank from the partially completed orthosis, plus a grind line indicator 48 and a drill hole 50. The grind line indicator 48 and drill hole 50 aid in formation of the orthosis.

Figure 5A:
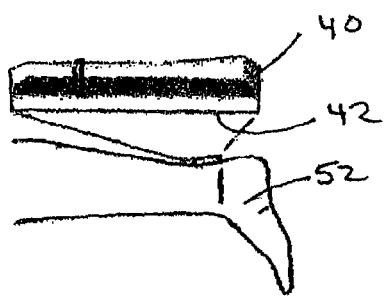
FIG. 5A is a side plan view of the molding blank of FIG. 4A positioned on a model of a leg prior to casting an orthosis.
Figure 5B:
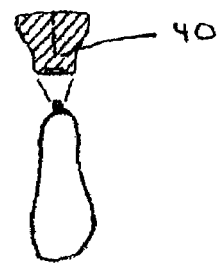
FIG. 5B is a bottom plan view of the molding blank of FIG. 5A positioned on a model of a leg prior to casting an orthosis.
Figure 5C:
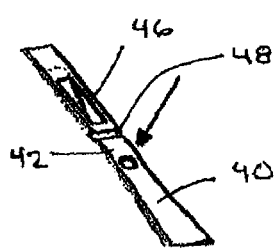
FIG. 5C is a perspective view of a molding plank positioned within a partially completed orthosis made in accordance with the invention.

The molding blank 40 can be used in accordance with methods of the invention to make an orthosis having a cavity for a bumper stem and having a bumper rest. A method of forming an orthosis 20 in accordance with the invention is depicted in FIGS. 5A through 5H. These figures also show various aspects of components used to form the orthosis 20, plus intermediate elements of the orthosis, and aspects of the finished orthosis. Referring now to FIG. 5A, the molding blank 40 is adhered to a foot model 52 of a patient being outfitted for the orthosis. Generally the foot model is encased in a stocking, onto which the molding blank 40 is glued. The narrow side 42 of the molding blank 40 is placed against the stocking. Thus, the tool slot 46 and grind line 48, for example, are pressed against the sock and not generally visible. The molding blank is preferably adhered to the foot model using a releasable adhesive, such as a rubber cement material. However, in other implementations this molding blank can be physically held in place, such as by hook and loop fasteners, and can be integrally formed with the molding blank. In such implementations the hook elements are typically formed in only the portion of the molding blank that comes in contact with the sock, and preferably only the upper portion of the molding blank has hooks because this portion of the molding blank is eventually discarded.

The molding blank 40 is placed on the foot mold in a position giving consideration to the eventual site of the motion stop. In most implementations the molding blank will be placed such that the finished motion stop and bumper rest are both above the back of a typical shoe worn by a person who would be wearing the orthosis. Although the precise position can vary, it is desirable to have the bottom of the molding blank 40 be positioned above the bottom of the ankle joint in the orthosis. In most implementations it is also desirable that the bottom of the molding blank be positioned above the axis of the ankle joint in the orthosis. An orthosis normally has the axis of the orthosis align substantially with the axis of the patient's ankle. Thus, in most implementations the molding blank 40 is arranged such that it is above, or even with, the axis of the ankle joint of the orthosis and the patient.

In some implementations the molding blank 40 can be positioned such that it extends below the axis of the ankle joint, although it is typically desirable to have the bottom of the molding blank be elevated as high as possible up above the bottom of the orthosis so as to avoid obstructing the shoe of a person wearing the orthosis. Thus, in some implementations the bottom of the molding blank is merely 0.25 inches above the axis of the ankle joint of the orthosis, while in other implementations the bottom of the molding blank is 0.50 inches or less above the axis, while in yet other implementations the bottom is 0.75 inches or less above the axis of the top axis of the orthosis.

Figure 5D:
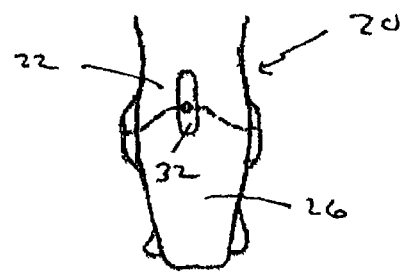
FIG. 5D is a posterior elevational view of a partially completed orthosis constructed in accordance with the invention.

Once the molding blank 40 is held in place, plastic used to form the upper 24 and lower 26 portions of the orthosis is vacuum formed around the molding blank 40 and around the foot mold 52. The plastic is typically a thermoformable sheet that can be vacuum-formed at elevated temperatures and then allowed to cool before being removed from the mold. Upon removal of the partially completed orthosis from the mold, the molding blank is typically retained on the orthosis, and is actually tightly secured to the orthosis because the configuration of the molding blank is such that the orthosis walls partially surround the molding blank The next step in completion of the orthosis 20 is generally cutting the molded orthosis into its upper and lower portions. Various saws and cutting tools are suitable for this purpose. In general the cut should follow proximate the middle or lower portion of the molding blank and on to the ankle joint. Here, in general, the center of the ankle joint is below the center of the molding blank, so the cut line across the orthosis 20 is higher in the posterior than it is along the sides of the orthosis, as shown in FIG. 5D. At this point the lower portion 26 of the orthosis has a substantially complete bumper rest 32 for the stopping bumper 30, this bumper rest 32 being formed from a combination of the retained lower segment of the molding blank, plus the portion of the plastic wall of the orthosis that surrounds and encapsulates much of this lower segment. It will be appreciated that, even though the lower portion 26 is suitable for use at this time, additional grinding and adjustment in the lower portion 26 can be performed, such as to smoothen the bumper rest 32, or (in some implementations) to remove the lower segment of the molding blank so as to insert an additional motion stop.

Figure 5E:
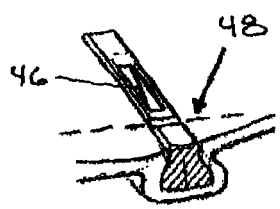
FIG. 5E is an enlarged perspective view of the top of a partially completed two-piece articulating orthosis after the top portion and bottom portion have been separated from one another, but before excess portions of the orthosis have been removed.
Figure 5F:
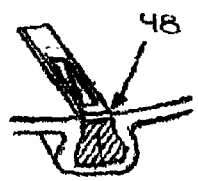
FIG. 5F is an enlarged perspective view of the top of an orthosis after the top portion and bottom portion have been separated from one another, and after excess portions of the orthosis have been removed.

Once the upper and lower portions of the orthosis have been separated from one another it is generally desirable to grind down or cut away part of the upper portion 22 of the orthosis. As shown in FIGS. 5E and 5F the grind line can serve as an indicator of how much of the molding blank should be removed in order to properly place a motion stop in the cavity formed by the molding blank.

Figure 5G:
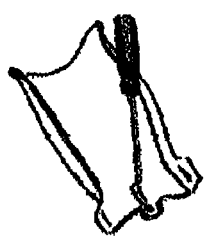
FIG. 5G is a perspective view showing removal of the molding blank from the top section of the orthosis.
Figure 5H:
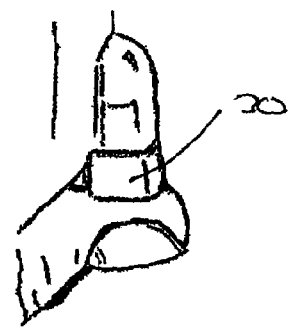
FIG. 5H is a perspective view of a stopping bumper being inserted into a channel in the top portion of an orthosis.

Referring now to FIG. 5G, a screwdriver or other tool can be used to force the top of the molding blank out of the top portion of the orthosis. This is done, for example, by using a straight blade of the screwdriver to apply pressure into the slot 46 formed in the molding blank. After the top of the molding blank is removed, a stopping bumper 30 can be inserted into the exposed cavity, as shown in FIG. 5H.

Figure 7:
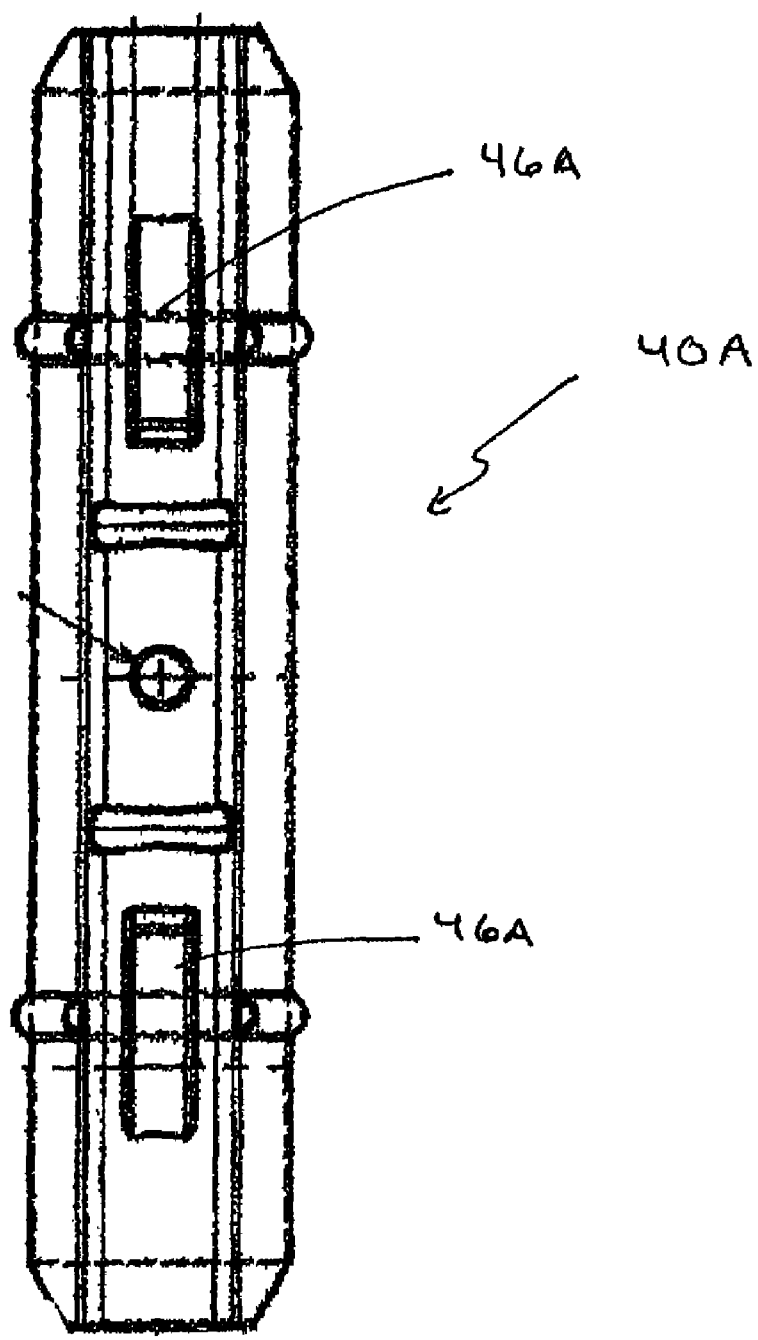
FIG. 7 is a perspective view of a molding blank constructed in accordance with an implementation of the invention.
Figure 8A:
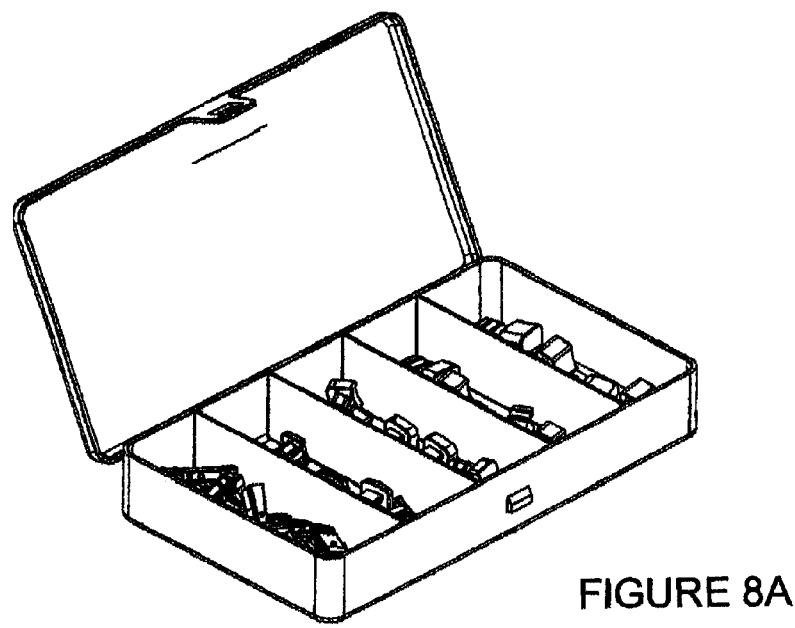
FIG. 8A is a perspective view of a plantar stop kit constructed and arranged in accordance with the present invention.
Figure 8B:
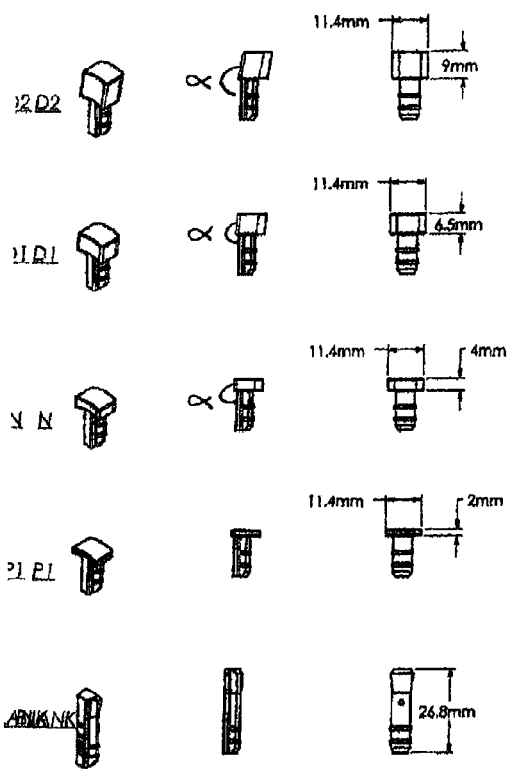
FIG. 8B is a plurality of views of stopping bumpers from the plantar stop kit of FIG. 8A.

Referring briefly now to FIG. 7, it will be appreciated that molding blanks made in accordance with the invention can also be configured so that both ends will be removed from the orthosis, typically so as to allow two stopping bumpers to be installed. FIG. 7 shows molding blank 40a with two tool slots 46A, each corresponding to a separate half of the molding blank that can be removed after cutting the upper and lower portions of the orthosis apart.

Figure 6A:
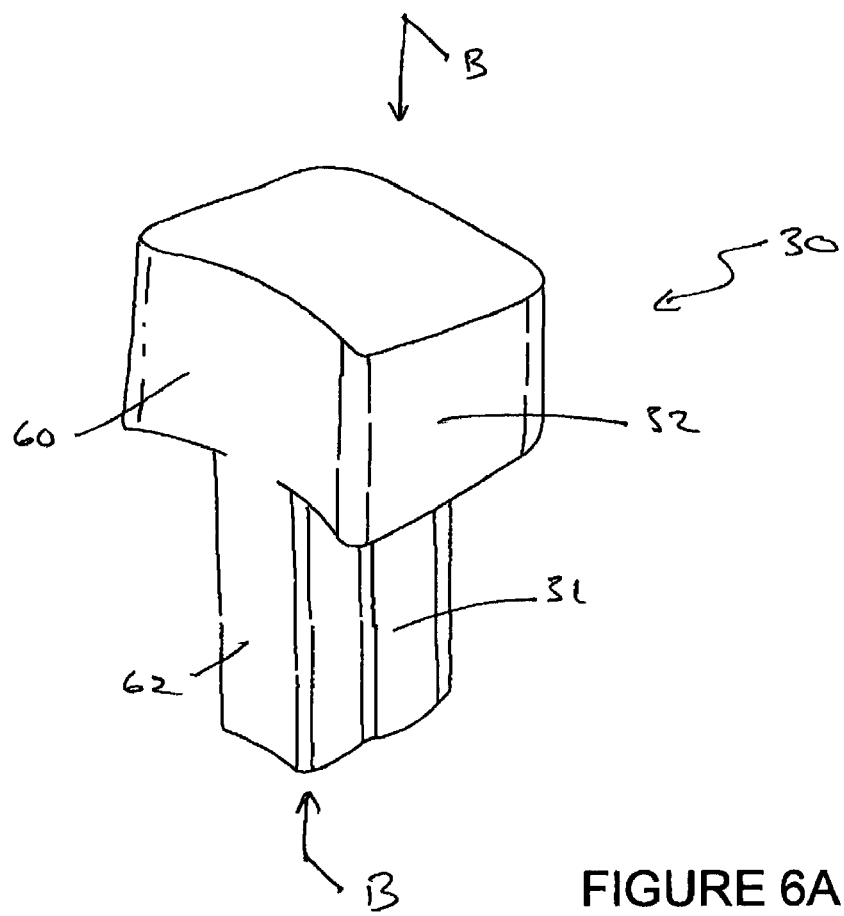
FIG. 6A shows an enlarged perspective view of a stopping bumper for a plantar flexion stop made in accordance with an implementation of the invention.
Figure 6B:
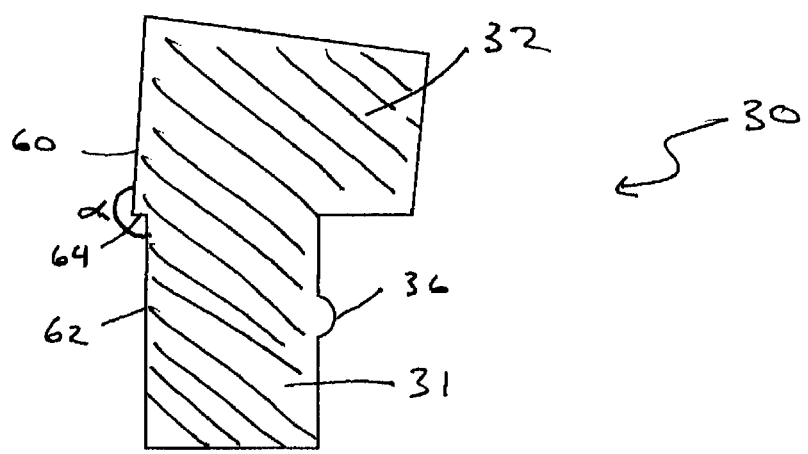
FIG. 6B enlarged cross sectional view of the motion stop of FIG. 6A, the cross section taken along line B—B of FIG. 6A.

In reference now to FIGS. 6A and 6B, various additional aspects of the motion stop are shown. The bumper head is normally larger than the bumper stem, having a much larger cross sectional area. Thus, the bumper head often overlaps the top of the stem, at least on three quarters of the perimeter of the stem. The bumper head also normally overlaps the bumper stem by a distance corresponding closely to the thickness of the wall of the orthosis. The benefit of this selection is that the head then corresponds substantially to the perimeter of the bumper rest. For example, in some implementations the bumper head overlaps the stem on at least three sides by a distance within 20 percent of the average thickness of the wall forming the cavity of the orthosis, while in other implementations this overlap is within 10 percent, and yet in other implementations this overlap is within 40 percent of the average thickness of the wall forming the cavity in the orthosis.

In general the stem of the bumper stop is configured to be at least partially exposed on the inside of an orthosis when the stem is installed in the orthosis. For example, the stem can be configured such that it fits into a cavity surrounding less than 330 degrees of perimeter of the stem, wherein the degrees are calculated from the approximate center of the stem. In other implementations the stem is configured such that it fits into a cavity surrounding less than 300 degrees around the perimeter of the stem.

Although the head and stem often have a significant overlap on at least three quarters of their circumferences, in some implementations the overlap of the head over the stem is significantly less, or even zero, on the anterior side of the stop (that portion facing against a patient and into the interior of the orthosis. Thus, in some implementations the stop mechanism has a stem with a surface 60 configured to face the inside of an orthosis; and a head having a surface 62 configured to face the inside of an orthosis, wherein the two surfaces of the stem and head are substantially continuous or flat. In other implementations there is some overlap 64 of the head onto the stem on the side of the stop that is proximate the interior of the orthosis. For example, this offset or overlap can be less than 5 millimeters, normally less than 4 millimeters, more typically less than 3 millimeters, desirably less than 2 millimeters, and even more desirably less than 1 millimeter.

Similarly, the stop mechanism can have a bumper head with a horizontal cross section with an area at least 50 percent greater than the horizontal cross section of the stem, the cross sections taken at substantially the vertical center of each of the head and stem. In some implementations the bumper head has a horizontal cross section at least 100 percent greater than the horizontal cross section of the stem, the cross sections taken at substantially the vertical center of each of the head and stem.

Various materials are suitable for use with the present invention to form the stopping bumper, including various plastics and thermoplastics. However, the materials used must be able to withstand significant repeat compressive forces without failure. In particular, it is important that the material survive these compressive forces so that the bumper head size can be kept as small as possible while still promoting consistent contact between the bumper head and bumper rest. In addition, the material must be readily formed into the bumper stop, typically by injection molding. A further general criteria is that the bumper head should not be so hard as to create a loud clicking sound when the head comes in contact with the bumper rest. Such loud sounds are common with metallic stops, but are desirably eliminated.

In some embodiments the bumper head comprises thermoplastic polyurethane with a Shore hardness of at least 55D according to ASTM D 2240 (ISO 868), and in some implementations the bumper head comprises a thermoplastic polyurethane with a Shore hardness of at least 57D according to ASTM D 2240 (ISO 868). The amount of deflection is also desirably reduced without sacrificing other parameters, such as durability and quietness. In some implementations the bumper head comprises thermoplastic polyurethane having less than 10 percent deflection at 1500 pounds per square inch of compressive load according to ASTM D575, or having less than 15 percent deflection at 1500 pounds per square inch of compressive load according to ASTM D575. Alternatively, in some implementations the thermoplastic polyurethane used to produce the stopping bumper has less than 20 percent deflection at 1500 pounds per square inch of compressive load according to ASTM D575. The bumper head may comprise thermoplastic polyurethane having less than 10 percent deflection at 1000 pounds per square inch of compressive load according to ASTM D575.

In certain implementations the bumper head comprises a polyester-based polyurethane having a flexural modulus of less than 50,000 pounds per square inch at a temperature of 23 degrees Celsius using ASTM D790 (ISO 178), more typically less than 40,000 pounds per square inch, and even more typically less than 37,000 pounds per square inch. Similarly, the bumper head typically comprises a polyurethane having a flexural modulus of greater than 15,000 pounds per square inch at a temperature of 23 degrees Celsius using ASTM D790 (ISO 178), and more commonly greater than 20,000 pounds per square inch. Thus, in certain embodiments the bumper head comprises a polyester-based polyurethane having a flexural modulus of less than from 25,000 to 30,000 pounds per square inch at a temperature of 23 degrees Celsius using ASTM D790 (ISO 178).

Specific suitable compositions used to form the stopping bumper include, for example, mixtures of Texin™ 255 and Texin™ 260 thermoplastic polyurethanes manufactured by Bayer and available from Bay State Polymer Distribution of Westlake, Ohio. Generally such compositions can contain at least 40 percent of each Texin™ polyurethane. In certain implementations the composition contains from 40 to 60 percent Texin™ 255 and from 40 to 60 percent Texin™ 260. In alternative implementations the composition contains from 50 to 70 percent Texin™ 255 and from 30 to 50 percent Texin™ 260. In yet other implementations the composition contains approximately 60 percent Texin™ 255 and 40 percent Texin™ 260.

The invention is further directed to a kit for forming an adjustable stop for an ankle-foot orthosis, the kit comprising a plurality of bumpers, each bumper having a head and a stem, the head and stem of each bumper forming an interface angle between an interior surface of the head and an interior surface of the stem. In addition, the plurality of bumpers can have multiple different head thicknesses, wherein the interface angle alpha between the interior surfaces is generally less for shorter heads than for thicker heads. Using a greater interface angle in the taller heads assures that they will properly seat on the stop bumper at the same location as shorter heads.

In general, motion stops made in accordance with the invention comprise a single removable bumper that comes in contact with a bumper rest that is not removable. However, in certain embodiments it is possible to use two removable bumpers configured to contact one another at a bumping interface without the use of a non-removable bumper rest. These dual-bumper implementations are particularly useful for applications where a patient wishes to have different stops for different activities. For example, a single bumper can be used by day to allow some plantar flexion, but two bumpers can be used at night to promote gastroc stretch.

The invention also includes methods of providing medical treatment using the improved ankle-foot orthosis. In general, one method of using the orthosis is to provide an ankle-foot orthosis having two cavities configured for receiving stems of a bumper stop, inserting a first bumper stop in the a first of the two cavities for a first period of time, inserting a second bumper stop into either the first or second of the two cavities for a second period of time, and repeating the final steps at regular intervals. This method can be used, for example, to promote gastroc stretch by having larger bumper stops, or two bumper stops, placed in the orthosis at night, while removing one or both of the stops (or replacing them with smaller stops) during the day.

The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the instant specification.

I claim:

1. A method of making an ankle-foot orthosis, the method comprising:
   providing a thermoformable material;
   providing a mold;
   providing a molding blank between the thermoformable material and the mold;
   thermoforming the thermoformable material to create an ankle-foot orthosis partially surrounding the molding blank;
   removing the molding blank to form a cavity; and
   inserting a removable stopping bumper into the cavity, the bumper configured to contact a bumper rest, the removable stopping bumper comprising a head and a stem, the head configured to contact the bumper rest, the stem configured for insertion into a cavity in an orthosis, wherein the bumper head has a larger horizontal cross section than the bumper stem; and wherein the bumper head overlaps the stem on at least three sides.

2. The method of claim 1, wherein the molding blank is at least partially accessible within an interior of the ankle-foot orthosis immediately after thermoforming of the orthosis.

3. The method of claim 1, further comprising cutting the ankle-foot orthosis into two parts along a cut line passing through the partially surrounded molding blank to separate the molding blank into two pieces.

4. The method of claim 3, further comprising removing one of the pieces of the molding blank.

5. The method of claim 3, wherein the molding blank has at least one tool-receiving recess or protrusion on the side of the molding blank that was facing the mold during thermoforming of the orthosis.

6. The method of claim 3, further comprising engaging the tool-receiving recess or protrusion on the side of the molding blank that was facing the mold during thermoforming of the orthosis so as to remove at least one of the pieces of the molding blank.

7. The method of claim 4, further comprising inserting a removable stopping bumper into a cavity formed from removal of a piece of the molding blank.

* * * * *